US010602957B2

(12) United States Patent
Thomas

(10) Patent No.: US 10,602,957 B2
(45) Date of Patent: Mar. 31, 2020

(54) SYSTEMS AND METHODS FOR DETECTING AND VISUALIZING BIOFIELDS WITH NUCLEAR MAGNETIC RESONANCE IMAGING AND QED QUANTUM COHERENT FLUID IMMERSION

(71) Applicant: VARUNA BIOMEDICAL CORPORATION, Incline Village, NV (US)

(72) Inventor: Stanton Thomas, Incline Village, NV (US)

(73) Assignee: VARUNA BIOMEDICAL CORPORATION, Incline Village, NV (US)

(*) Notice: Subject to any disclaimer, the term of this patent is extended or adjusted under 35 U.S.C. 154(b) by 510 days.

(21) Appl. No.: 14/930,516

(22) Filed: Nov. 2, 2015

(65) Prior Publication Data

US 2017/0000379 A1    Jan. 5, 2017

Related U.S. Application Data

(60) Provisional application No. 62/187,045, filed on Jun. 30, 2015, provisional application No. 62/203,760, filed on Aug. 11, 2015.

(51) Int. Cl.
*A61B 5/055* (2006.01)
*G01R 33/50* (2006.01)
(Continued)

(52) U.S. Cl.
CPC ............ *A61B 5/0555* (2013.01); *A61B 5/055* (2013.01); *A61B 5/7267* (2013.01); *A61B 5/742* (2013.01);
(Continued)

(58) Field of Classification Search
CPC .... G01N 24/08; G01N 24/081; G01N 24/082; G01N 24/084; G01R 33/24; G01R 33/62
See application file for complete search history.

(56) References Cited

U.S. PATENT DOCUMENTS 3,789,832 A    2/1974  Damadian
3,932,805 A    1/1976  Abe et al.
(Continued)

FOREIGN PATENT DOCUMENTS

CN    1112328 C    6/2003
EP    979424 A1    12/1997
(Continued)

OTHER PUBLICATIONS

Noninvasive liver iron measurements with a room-temperature susceptometer; pub. Physiol Meas. Apr. 2007 ; 28(4): 349-361. doi: 10.1088/0967-3334/28/4/002. by. W F Avrin and S Kumar (Year: 2007).*
(Continued)

*Primary Examiner* — Katherine L Fernandez
*Assistant Examiner* — Michael S Kellogg
(74) *Attorney, Agent, or Firm* — Shay Glenn LLP

(57) ABSTRACT

Systems and methods for imaging and detecting the biofield of a living subject are provided. A biofield detection system can include a number of features, including a nuclear magnetic resonance imaging system, a fluid container configured to hold a fluid and the living subject, and a fluid management system configured to enhance a coherence of the fluid volume. The biofield detection system can implement a biofield detection scheme that compares a baseline NMR image of the fluid in the absence of the subject to a NMR image of the fluid surrounding the subject. The two images can be compared and analyzed to detect variances relating to field effects of the subject. Systems and methods
(Continued)

are also provided in which environmental factors can be introduced to the fluid volume or the living subject. Subsequent detection scans can detect changes in the biofield based on the introduction of environmental factors.

10 Claims, 8 Drawing Sheets

(51) Int. Cl.
*A61B 5/00* (2006.01)
*G01N 24/08* (2006.01)
*G01R 33/38* (2006.01)

(52) U.S. Cl.
CPC ......... *G01N 24/08* (2013.01); *G01R 33/3806* (2013.01); *G01R 33/50* (2013.01)

(56) References Cited

U.S. PATENT DOCUMENTS

| | | |
|---|---|---|
| 4,021,726 A | 5/1977 | Garroway et al. |
| 4,222,658 A | 9/1980 | Mandel |
| 4,254,778 A | 3/1981 | Clow et al. |
| 4,328,809 A | 5/1982 | Hirschowitz et al. |
| 4,398,148 A | 8/1983 | Barjhoux et al. |
| 4,429,288 A | 1/1984 | Gelinas |
| 4,528,508 A | 7/1985 | Vail |
| 4,573,014 A | 2/1986 | Riederer |
| 4,576,777 A | 3/1986 | Weber |
| 4,602,639 A | 7/1986 | Hoogendoorn et al. |
| 4,642,568 A | 2/1987 | Young |
| RE32,619 E | 3/1988 | Damadian |
| 4,788,427 A | 11/1988 | LeRoy |
| 4,942,884 A | 7/1990 | Ichinomiya et al. |
| 5,168,224 A | 12/1992 | Maruizumi et al. |
| 5,318,031 A | 6/1994 | Mountford et al. |
| 5,417,211 A | 5/1995 | Abraham Fuchs et al. |
| 5,441,495 A | 8/1995 | Liboff et al. |
| 5,479,925 A | 1/1996 | Dumoulin et al. |
| 5,646,532 A | 7/1997 | Knuttel et al. |
| 6,016,450 A | 1/2000 | Crock |
| 6,023,162 A * | 2/2000 | Johnson ............ G01R 33/4822 324/300 |
| 6,177,794 B1 | 1/2001 | Stoeffl |
| 6,187,032 B1 | 2/2001 | Ohyu et al. |
| 6,236,210 B1 | 5/2001 | Takekoshi et al. |
| 6,336,043 B1 | 1/2002 | Suzuki et al. |
| 6,347,238 B1 | 2/2002 | Levengood et al. |
| 6,466,688 B1 | 10/2002 | Ramstack |
| 6,592,611 B1 | 7/2003 | Zawada |
| 6,645,144 B1 | 11/2003 | Wen et al. |
| 6,675,047 B1 | 1/2004 | Konoplev et al. |
| 6,746,397 B2 | 6/2004 | Lee et al. |
| 6,807,438 B1 | 10/2004 | Brun Del Re et al. |
| 7,078,911 B2 | 7/2006 | Cehelnik |
| 7,225,812 B2 | 6/2007 | Nedeljkovic et al. |
| 7,363,070 B2 | 4/2008 | Ogata et al. |
| 7,382,128 B2 | 6/2008 | Bulkes et al. |
| 7,511,502 B2 | 3/2009 | Sakakura et al. |
| 7,551,957 B2 | 6/2009 | Whelan et al. |
| 7,840,250 B2 | 11/2010 | Tucker |
| 7,885,700 B2 | 2/2011 | Clark et al. |
| 7,983,743 B2 | 7/2011 | Rudy et al. |
| 8,188,733 B2 | 5/2012 | Lausch et al. |
| 8,195,273 B2 | 6/2012 | Trequattrini et al. |
| 8,295,903 B2 | 10/2012 | Eckert et al. |
| 8,306,265 B2 | 11/2012 | Fry et al. |
| 8,811,692 B2 | 8/2014 | Prokoski |
| 9,105,958 B2 | 8/2015 | Suddath |
| 2002/0035358 A1 | 3/2002 | Wang |
| 2004/0162597 A1 | 8/2004 | Hamilton et al. |
| 2005/0030026 A1 | 2/2005 | Pines et al. |
| 2006/0272624 A1 | 12/2006 | Pettersson |
| 2007/0187327 A1 | 8/2007 | George et al. |
| 2007/0238092 A1 | 10/2007 | Rubesa |
| 2007/0287881 A1 | 12/2007 | Akimov et al. |
| 2009/0156659 A1 | 6/2009 | Butters et al. |
| 2010/0100163 A1 | 4/2010 | Lee |
| 2010/0161010 A1 | 6/2010 | Thomas |
| 2010/0323391 A1 | 12/2010 | Montagnier et al. |
| 2011/0201932 A1 | 8/2011 | Duric et al. |
| 2012/0015177 A1 | 1/2012 | Kim |
| 2013/0044210 A1 | 2/2013 | Rozenboim et al. |
| 2013/0100000 A1 | 4/2013 | Reavis et al. |
| 2013/0158387 A1 * | 6/2013 | Tanttu ................ G01R 33/4804 600/411 |
| 2013/0253302 A1 | 9/2013 | Eckert et al. |
| 2014/0288621 A1 | 9/2014 | Efremkin |
| 2016/0129278 A1 | 5/2016 | Mayer |

FOREIGN PATENT DOCUMENTS

| | | |
|---|---|---|
| EP | 1962151 A1 | 8/2008 |
| EP | 2140311 A2 | 1/2010 |
| WO | WO96/041872 A1 | 12/1996 |
| WO | WO2007/068831 A2 | 6/2007 |
| WO | WO2007/071855 A2 | 6/2007 |
| WO | WO2007/107689 A1 | 9/2007 |
| WO | WO2008/145957 A2 | 12/2008 |
| WO | WO2014/006598 A1 | 1/2014 |

OTHER PUBLICATIONS

Baffa et al.; Magnetic and electric characteristics of the electric fish *Gymnotus carapo*; Biophys. J. 63(2); pp. 591-593; Aug. 1992.

Bedore et al.; Bioelectric fields of marine organisms: voltage and frequency contributions to detectability by electroreceptive predators; Physiol. Biochem. Zool.; 86(3); pp. 298-311; Jun. 1986.

Bischoff et al.; Communication and the emergence of collective behavior in living organisms: a quantum approach; Mol. Biol. Int.; vol. 2013; 19 pages; Oct. 30, 2013.

Chaplin; Anomalous properties of water, water structures and science; 6 pages; Jan. 13, 2016 retrieved from the Internet (http://www.lsbu.ac.uk/water/water_anomalies.html).

Cohen et al.; Biophoton emission of human body; Indian J. Exp. Biol.; 41(5); pp. 440-445; May 2003.

Davidson et al.; Biological water dynamics and entropy: a biophysical origin of cancer and other diseases; Entropy; 15; pp. 3822-3876; Sep. 13, 2013.

De Ninno; The influence of the magnetic field on the kinetic of the chemical reaction; (preseantation slides); (ENEA) Italian National Agency for New Technologies, Energy and Sustainable Economic Development; Pamporovo, Bulgaria; 36 pages; Oct. 9-12, 2014.

Del Giudice et al.; Water dynamics at the root of metamorphosis in living organisms; Water; 2; pp. 566-586; Sep. 3, 2010.

Bono et al.; Emergence of the coherent structure of liquid water; Water; 4(3); pp. 510-532; Jul. 9, 2012.

Dibble et al.; Bulk water with exclusion zone water charateristics: experimental evidence of interaction with a non-physical agent; Water; 6; pp. 35-44; Mar. 20, 2014.

Gang et al.; Water dynamics following treatment by one hour 0.16 tesla static magnetic fields depend on exposure volume; Water; 3; pp. 122-131; Feb. 12, 2012.

Giuliani et al.; eds.; Non-thermal effects and mechanisms of interaction between electromagnetic fields and living matter; National Institute for the study and Control of Cancer and Enviromental Diseases "Bernardino Ramazzini"; Bologna, Italy; 2010; European J. of Oncology; 5; pp. 1-217; Jan. 14, 2016 retrieved from the internet (http://www.icems.eu/papers/ramazzini_library5_part1.pdf).

Hammerschlag et al.; Biofield research: a roundtable discussion; The J. Altern. Complement. Med.; 18(12); pp. 1081-1086; Dec. 2012.

Ho; Illuminating water and life; Entropy; 16; pp. 4874-4891; Sep. 10, 2014.

Ho; Super-conducting liquid crystalline water aligned with collagen fibres in the fascia as acupuncture meridians of traditional chinese medicine; Forum on Immunopathological Diseases and Therapies;

(56) References Cited

OTHER PUBLICATIONS

3(3-4); pp. 221-236; (year of pub. sufficiently earlier than effective US filing date and any foreign priority date) 2012.

Hopkins et al.; Design features for electric communication; J. Exp. Biol.; 202 (Pt 10); pp. 1217-1228; May 1999.

Kobayashi et al.; Imaging of ultraweak spontaneous photon emission from human body displaying diurnal rhythm; PLoS ONE; 4(7); e6256; 8 pages; Jul. 16, 2009.

Lo et al.; Evidence for the existence of stable-water-clusters at room temperature and normal pressure; Physics Letters A; 373(42); pp. 3872-3876 Aug. 2009.

Montagnier et al.; DNA waves and water; J. of Physics: Conf. Series; 306 (1); 10 pages; Jul. 8, 2011.

Ozeki; Water interacting with magnetic fields: structures, properties, and functions; Conference on the physics, Chemistry and Biology of Water; Water Conference 2013; 1 page; Jan. 14, 2016 retrieved from the internet (http://www.waterconf.org/participants-materials/2013/abstracts/Sumio%20Ozeki%20%20Abstract.pdf) (Abstract Only).

Popp; Properties of biophotons and their theoretical implications;Indian J. Exp. Biol.; 41(5); pp. 391-402; May 2003.

Popp et al.; Evidence of non-classical (squeezed) light in biological systems; Physics Letters; 293; pp. 98-102; Jan. 21, 2002.

Rein; Biological effects of quantum fields and their role in the natural healing process; Frontier Perspectives; 7; pp. 16-23; (year of pub. sufficiently earlier than effective US filing date and any foreign priority date) 1998.

Rein; Bioinformation within the biofield: beyond bioelectromagnetics; J. Altern. Complement. Med.; 10(1); pp. 59-68; Feb. 2004.

Richter et al.; Intermolecular multiple quantum coherences in liquids; Concepts in Magnetic Resonance; 12(6); pp. 396-409; Jan. 1, 2000.

Rubik; Measurement of the human biofield and other energetic instruments; Mosby's complementary & alternative medicine: a research-based approach; Edition 3; Chap. 20; 37 pages; Jun. 9, 2008.

Smith; Quanta and coherence effects in water and living systems; J. of Altern. Complement. Med.; 10(1); pp. 69-78; Feb. 2004.

Szasz et al.; Do field-free electromagnetic potentials play a role in biology?; Electromagnetic Biology and Medicine; 28; pp. 135-147; Jan. 1, 2009.

Tedeschi; Is the living dynamics able to change the properties of water; Int. J. of Design & Nature and Ecodynamics; 5(1); pp. 60-67; (year of pub. sufficiently earlier than effective US filing date and any foreign priority date) 2010.

Tiller; What are subtle energies; Journal of Scientific Exploration; 7(3); pp. 293-304; (year of pub. sufficiently earlier than effective US filing date and any foreign priority date) 1993.

Van Wijk; Bio-photons and bio-communication; Journal of Scientific Exploration; 15(2); pp. 183-197; (year of pub. sufficiently earlier than effective US filing date and any foreign priority date) 2001.

Zhang et al.; Experimental characterization of intermolecular multiple-quantum coherence pumping efficiency in solution NMR; J. of Magnetic Resonance; 148(1); pp. 200-208; Jan. 31, 2001.

Zheng et al.; Surfaces and interfacial water: evidence that hydrophilic surfaces have long-range impact; Adv. In Colloid. and Interface Science; 127(1); pp. 19-27; Nov. 23, 2006.

Thomas; U.S. Appl. No. 16/471,663 entitled "Systems and methods for biomodulation using a fluis immersion pathway and photo-induced coherent resonance energy transfer," filed Jun. 20, 2019.

\* cited by examiner

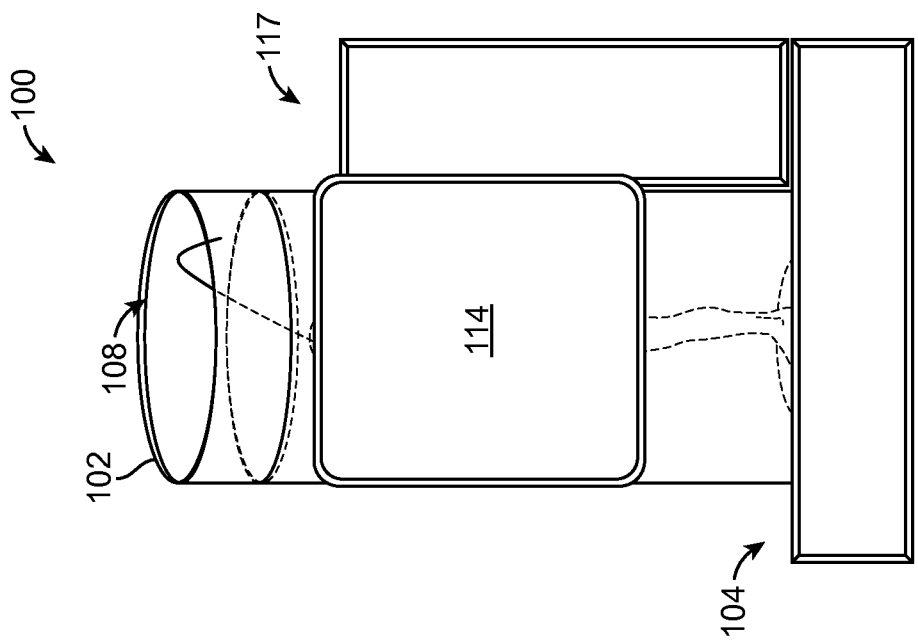
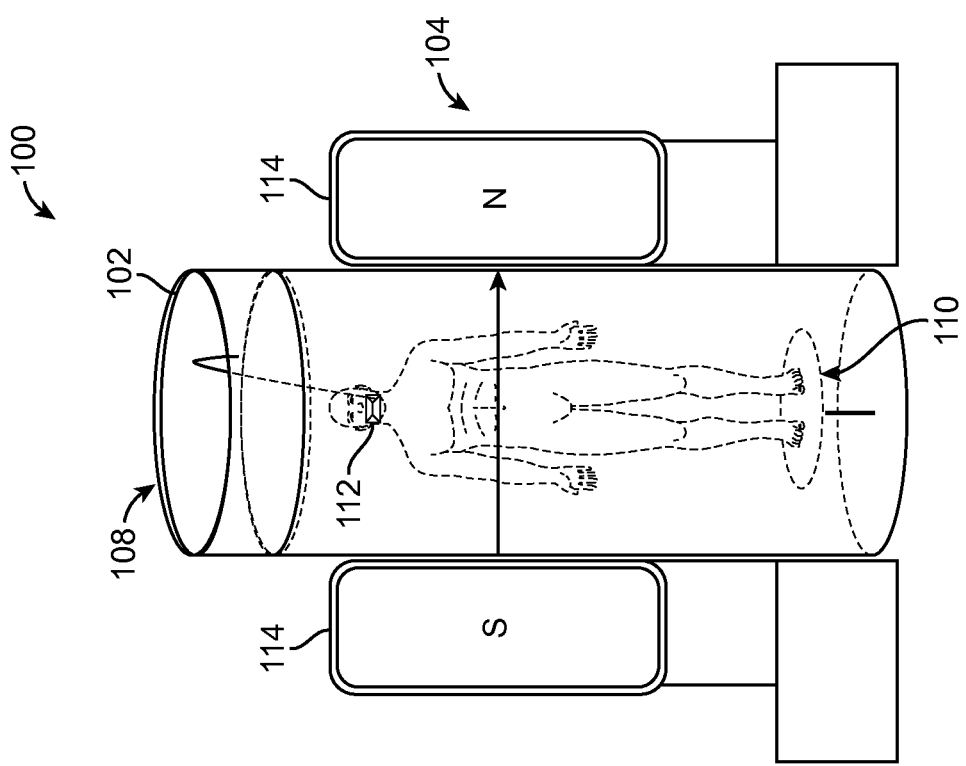
FIG. 1A
FIG. 1B

Biofield changes isolated and highlighted

Comparison Rendering

SYSTEMS AND METHODS FOR DETECTING AND VISUALIZING BIOFIELDS WITH NUCLEAR MAGNETIC RESONANCE IMAGING AND QED QUANTUM COHERENT FLUID IMMERSION

CROSS REFERENCE TO RELATED APPLICATIONS

This application claims the benefit of U.S. Provisional Appln. No. 62/187,045, titled "Systems and Methods for Detecting and Visualizing Biofields with Nuclear Magnetic Resonance Imaging", filed Jun. 30, 2015, and also claims the benefit of U.S. Provisional Appln. No. 62/203,760, titled "Systems and Methods for Detecting and Visualizing Biofields with Nuclear Magnetic Resonance Imaging and QED Quantum Coherent Fluid Immersion", filed Aug. 11, 2015.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to detecting energetic fields or biofields emitted from living organisms. More specifically, this disclosure provides systems and methods for detecting, measuring, visualizing, and characterizing structures, anomalies, and bi-directional interactions relative to the biofield of a living organism via immersion within a quantum coherent liquid bio-communication pathway and Nuclear Magnetic Resonance Imaging (NMRI).

BACKGROUND

Since the discovery of Nuclear Magnetic Resonance (NMR) in 1938 and the subsequent expansion of the technique in 1946, much of the innovation in this field has occurred in the area applications relating to NMRI. When NMRI was discovered in 1971, it spawned a generation of development related primarily to apparatus and methods for medical imaging of the internal anatomical structure and environment of human and animal bodies for research and diagnostic purposes.

In the field of Complementary and Alternative Medicine (CAM) there is a growing understanding that living organisms are not merely biochemical machines comprised of functional components, but that they are also energetic systems that exchange energy and information with their environment. This energetic exchange appears to directly influence and reflect the health and vitality of living systems.

A biofield can generally be defined as the energy fields that surround, permeate, penetrate, and are emitted by the body of a living organism. A living organism can include humans, animals, bacterium, and plants. These energy fields can include electric, magnetic, electromagnetic fields, field potentials such as magnetic vector potentials and/or electrostatic potentials, acoustic energy, and non-classical quantum fields. After almost 100 years of scientific research, the biofield remains difficult to fully characterize as it is likely comprised, in part, by non-classical fields that are not directly observable by scientists.

Research into how biofields of living organisms interact with their environment, and how biofields reflect the dynamics of internal biological processes can produce profound new insights related to health and healing. Such insights may show how biofield anomalies are indicators of disease, infection and other conditions before they are manifested physically within the body. Uniquely identifiable energetic signatures in the biofield may be precursors of both the onset, and the healing, of specific physical and/or mental health conditions in humans. With this understanding the development of effective healing modalities may be facilitated based upon therapeutic interaction with the biofield itself.

Water possesses unique properties, being the only chemical compound that occurs naturally and in abundance on Earth in all three common phases: gas, liquid, and solid. Water displays an impressive array of anomalous properties in its physical, material, phase, density, and thermodynamic characteristics. Water is highly interactive with its surrounding environment, engaging in electrostatic interactions with other dipoles and ions and rapidly forming hydrogen bonds, as both donor and acceptor, with other water molecules and molecular compounds dissolved in water. The hydrogen bonding characteristic of the water molecule gives it enormous morphological flexibility. In its liquid form, water has been discovered to exist simultaneously in two states of different density and forms stable, geometric supramolecular structures or clusters of increasing phase coherence under ambient conditions. These quasi-crystalline structures are indeed predicted for liquid water under Quantum Electrodynamics (QED).

Under QED, quantum coherence in water arises from the fluctuations in the quantum vacuum and the interaction (coupling) of matter quantum fields with electromagnetic fields. Here, water molecules oscillate in unison between two single-particle states and trap a non-vanishing EM field in the ensemble, where phase correlations are held by the magnetic vector potential (A). The trapped EM field grows, attracting other molecules of the same species. The resulting stable (long-lived) cavities are called Quantum Coherence Domains, or CDs. The wavelength of the field is the size of the CD and its frequency is related to the energy level of the molecular ensemble (matter field). This self-producing CD formation among water molecules in a vapor state, under suitable conditions, achieves a runaway or avalanche process whereby the system is driven to saturation resulting in the phase transition to liquid. Then, according to QED, in its liquid state a plurality of coherent liquid water phases can coexist under the same thermodynamic conditions.

To date, there has been no published research or prior art citations relative to the use of NMRI devices and/or methods to detect the biofield emitted from, and surrounding, living organisms. The present disclosure provides a NMRI approach to biofield detection which embraces the idea that, as an energy field, the biofield interacts with matter and that resonance may be employed to observe its energetic signature around living organisms. Perhaps the most striking aspect of the novel use of NMRI in this disclosure is that it does not seek to characterize the internal anatomical and metabolic features of the organism at all, but instead focuses on the resonance of the nuclei surrounding it.

SUMMARY OF THE DISCLOSURE

A method of imaging a biofield surrounding a living subject is provided, comprising the steps of scanning a fluid volume with a nuclear magnetic resonance imaging system to produce a baseline dataset, scanning the fluid volume with the nuclear magnetic resonance imaging system while the living subject is disposed within the fluid volume to produce a detection dataset, comparing the detection dataset to the baseline dataset with a computing system to produce a biofield dataset that includes spatially-encoded, discrete variations in observed transverse relaxation time and/or relaxation rate in the fluid volume, and generating, with the computing system, an image of the biofield surrounding the living subject from the biofield dataset.

In some embodiments, the method further comprises identifying biofield anomalies from the image for diagnostic purposes. In other embodiments, the method further comprises cataloguing biofield anomalies from the image for diagnostic purposes. In additional embodiments, the method further comprises relating biofield anomalies from the image to known classifications for diagnostic purposes.

In some embodiments, the method further comprises identifying a disease in the living subject based on the image. In other embodiments, the method further comprises identifying an infection in the living subject based on the image. In alternative embodiments, the method further comprises identifying a physiological condition in the living subject based on the image. In additional embodiments, the method further comprises identifying a psychological condition in the living subject based on the image.

In one embodiment, the living subject comprises a human subject.

In some embodiments, the method further comprises introducing one or more environmental factors into the fluid volume, scanning the fluid volume with the nuclear magnetic resonance imaging system while the living subject is disposed within the fluid volume to produce a second detection dataset, comparing the baseline dataset to the second detection dataset with the computing system to produce a second biofield dataset that includes discrete variations in observed transverse relaxation time and/or relaxation rate in the fluid volume, and generating, with the computing system, a post-exposure image of the biofield surrounding the living subject from the biofield dataset.

In some embodiments, the method further comprises comparing the post-exposure image to the image to detect biofield variances before and after the introduction of the one or more environmental factors into the fluid volume.

In one embodiment, the one or more environmental factors are selected from the group consisting of man-made electromagnetic fields, naturally occurring electromagnetic fields, gases, liquids, aerosols, solids, chemical compounds, minerals, fabrics, crystals, foods, and medications. In other embodiments, the one or more environmental factors comprises a therapeutic and treatment modality.

In some embodiments, the method further comprises treating the fluid volume to increase a coherence of the fluid volume.

In additional embodiments, the method further comprises demagnetizing the fluid volume before scanning the fluid volume to produce the second detection dataset. In some embodiments, the method comprises demagnetizing the fluid volume before scanning the fluid volume to produce the second detection dataset.

In one embodiment, the method further comprises displaying the image of the biofield surrounding the living subject. In some embodiments, the method further comprises displaying the post-exposure image of the biofield surrounding the living subject.

In one embodiment, the baseline dataset is produced while the living subject is not disposed within the fluid volume. In some embodiments, the image of the biofield surrounding the living subject provides imaging information related only to the fluid volume surrounding the living subject, and does not provide imaging information related to anatomical details of the living subject.

A biofield detection system is also provided, comprising a fluid container sized and configured to hold a fluid surrounding a living subject, a nuclear magnetic resonance imaging (NMRI) system configured to produce a nuclear magnetic resonance image of the fluid within the fluid container; a computer controller configured to generate and control scanning sequences of the NMRI system, the computer controller being configured to perform a baseline scan of the fluid in the fluid container with the NMRI system to produce and store a baseline dataset, the computer controller being further configured to perform a detection scan of the fluid when the living subject is disposed in the fluid container with the NMRI system to produce and store a detection dataset, the computer controller being further configured to compare the baseline dataset to the detection dataset to produce a biofield dataset that includes variations in observed transverse relaxation time and/or relaxation rate in the fluid, and the computer controller being configured to generate a biofield image of the biofield surrounding the living subject, and a display configured to display the biofield image.

In one embodiment, the system further comprises a fluid management system including a storage tank and one or more pumps configured to pump fluid from the storage tank into the fluid container. In some embodiments, the fluid management system is configured to control a temperature of the fluid. In other embodiments, the fluid management system is configured to maintain a fluid level of fluid in the fluid container.

In another embodiment, the fluid management system further comprises a water conditioning unit configured increase a coherence of the fluid. In some embodiments, the water conditioning unit is adapted to add trace amounts of non-aqueous compounds to the fluid to increase the coherence of the fluid. In other embodiments, the water conditioning unit is configured to percolate the fluid through glass or quartz crystals to increase the coherence of the fluid.

In another embodiment, the fluid management system further comprises an outflow tank into which fluid from the fluid container can be pumped or drained.

In some embodiments, the fluid management system further comprises a demagnetizer unit configured to demagnetize fluid from the outflow tank to de-structure the fluid.

In an additional embodiment, the fluid management system further comprises a filtration system configured to filter the de-structured fluid.

In one embodiment, the NMRI system further comprises a plurality of main magnets, magnetic gradient coils, and RF coils. In other embodiments, the NMRI system comprises an open bore assembly. In some embodiments, the NMRI system can be adjusted between an open position that provides viewing and access to the fluid container and a closed position in which the NMRI system fully or partially encloses the fluid container.

In some embodiments, the living subject comprises a human subject.

In another embodiment, the biofield image provides imaging information related only to the fluid surrounding the living subject, and does not provide imaging information related to internal anatomical details of the living subject.

A biofield detection system is provided, comprising a fluid container sized and configured to hold a fluid and a living subject, a nuclear magnetic resonance imaging (NMRI) system configured to produce a static magnetic field within the fluid of the fluid container, and a computer controller configured to generate and control scanning sequences of the NMRI system to produce an image of the living subject's biofield in the fluid surrounding the living subject the fluid container.

In some embodiments, the living subject comprises a human subject.

In other embodiments, the computer controller does not produce an image of internal anatomical details of the living subject.

In one embodiment, the system further comprises a fluid management system including a storage tank and one or more pumps configured to pump fluid from the storage tank into the fluid container. In some embodiments, the fluid management system is configured to control a temperature of the fluid. In other embodiments, the fluid management system is configured to maintain a fluid level of fluid in the fluid container. In some embodiments, the fluid management system further comprises an outflow tank into which fluid from the fluid container can be pumped or drained. In other embodiments, the fluid management system further comprises a demagnetizer unit configured to demagnetize fluid from the outflow tank to de-structure the fluid. In additional embodiments, the fluid management system further comprises a filtration system configured to filter the de-structured fluid.

In alternative embodiments, the fluid management system further comprises a water conditioning unit configured increase a coherence of the fluid. In one embodiment, the water conditioning unit is adapted to add trace amounts of non-aqueous compounds to the fluid to increase the coherence of the fluid. In other embodiments, the water conditioning unit is configured to percolate the fluid through glass or quartz crystals to increase the coherence of the fluid.

In one embodiment, the NMRI system further comprises a plurality of main magnets, magnetic gradient coils, and RF coils. In other embodiments, the NMRI system comprises an open bore assembly. In additional embodiments, the NMRI system can be adjusted between an open position that provides viewing and access to the fluid container and a closed position in which the NMRI system fully or partially encloses the fluid container.

In one embodiment, the system further comprises a display configured to display the image of the living subject's biofield.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1B show one embodiment of a biofield detection system.

FIGS. 7A-7C show one embodiment of what images of a biofield surrounding a target subject from the biofield detection system may look like.

DETAILED DESCRIPTION

Figure 2A:
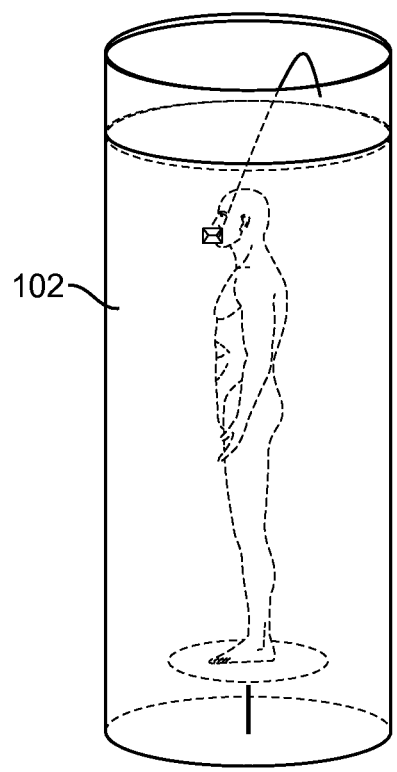
FIGS. 2A-2B show another embodiment of a fluid container of a biofield detection system.
Figure 2B:
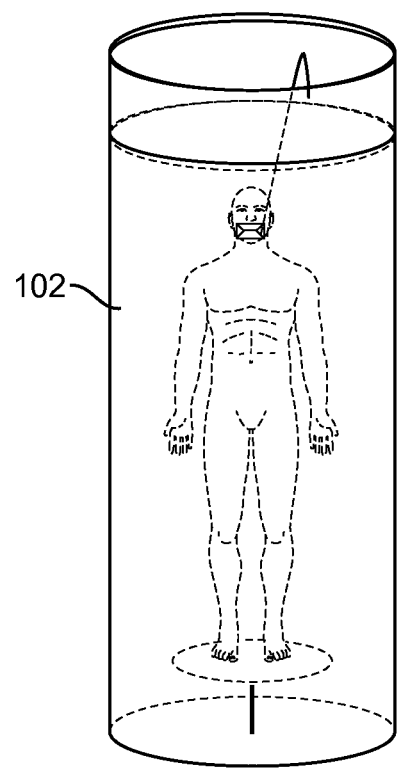

It is an objective of this disclosure to provide systems and methods for detecting and characterizing the complex bi-directional interactions of biofields emitted from living organisms with their environment for use in environmental, clinical, and medical research and diagnostics, as well as assessment of the efficacy of treatment and therapeutic modalities.

It is an objective of this disclosure to provide systems and methods for identifying and isolating environmental factors that either positively or negatively impact the biofields of living organisms. These environmental factors may include, but are not limited to, naturally-occurring and man-made environmental EMF and chemical compounds, aerosols, foods, plant matter, minerals, and crystals.

It is also an objective of this disclosure to provide a method for visualization and manipulation of biofield images, and for identifying and categorizing anomalies present in these images.

It is also an objective of this disclosure to provide systems and methods for facilitating diagnostics and the evaluation of treatments using biofield imaging by identifying, linking, and categorizing biofield anomalies with potential conditions and known causal factors.

It is also an objective of this disclosure to provide systems and methods for comparing and isolating the biological effects of various environmental exposures, directed thought and intention, and/or treatments based upon rendered biofield detection images.

It is an objective of this disclosure to further provide systems and methods for the assessment of the efficacy of existing treatment and therapeutic modalities that may involve conventional western medicine as well as Complimentary and Alternative Medicine (CAM). Such studies may also result in the development of new modalities.

The foundational ideas behind this novel approach to detecting or inferring the effects of the biofield include the known phenomenon of matter-energy interactions, and the superposition principle which provides a simplified theoretical model of field interactions. The novel approach to detecting and characterizing bi-directional interaction of a living organism's biofield with its environment and with treatment modalities further includes the phenomenon of Quantum Electrodynamics (QED) coherence in condensed matter and nuclear magnetic resonance.

The phenomenon of coherence within fluid, and liquid water in particular, plays a central role within the context of this disclosure. It is an objective of this disclosure to provide systems and methods that facilitate and enhance the bi-directional communication of bio-information between living systems and their environment. Local phase changes in fluid CDs induced by chemical reactions can be communicated across distant coherent regions by an underlying EM potential field, enabling long-range correlation without a transfer of energy. The present disclosure incorporates a specialized NMRI device operating in conjunction with a fluid immersion container and fluid management system to capture and visualize the living biofield, its interaction with various environmental factors, and its responsiveness to medical treatment and CAM healing modalities. In some embodiments, the fluid management system can enhance or modify the fluid volume to increase the coherence of the fluid volume.

Systems and methods are provided herein which isolate biofield effects by imposing a static magnetic field, magnetic field gradients, and using RF pulse sequences to excite atomic nuclei within a fluid volume surrounding a living organism during a detection scan. The observed transverse (spin-spin) relaxation response of the nuclei within the fluid volume can be measured, recorded, and processed. Computer algorithms can be implemented to compare the results of the detection scan to measurements obtained during a baseline scan of the fluid volume without the living organism. Subtle variations in response time, rate, and/or other signal characteristics between the two measurements can be attributable, in part, to the effects of biofields surrounding the living organism.

Systems and methods are also provided herein for introducing environmental factors into the fluid volume, or on, in, or near the living organism, to observe and study the effects on the biofield. These environmental factors can include naturally-occurring and man-made environmental EMF and chemical compounds, aerosols, foods, plant matter, minerals, and crystals. For example, samples of non-living matter can be encapsulated and positioned in proximity to the body, topically applied to the body, or inhaled, injected or ingested into the body of the living organism. In the case of environmental EMF, by example, a source of narrow-bandwidth filtered light can be directed at the organism from a location external to the wall of the fluid container.

Subsequent detection scans can be initiated after the introduction of environmental factors, the results of which can be compared to the initial detection scan. Changes in the biofield characteristics between the initial detection scan and subsequent post-exposure/treatment detection scans can be automatically identified, isolated, and visually highlighted. The successive detection scans and comparisons can be performed to evaluate temporal variations in specific biofield interaction effects.

According to the present disclosure, the focus of biofield detection and characterization using NMRI is phase coherence and the formation of supramolecular structures in aqueous solutions. To date, there has been no published research or prior art citations relative to the use of NMRI devices and/or methods to detect the biofield emitted from, and surrounding, living organisms. The same is true with regards to the idea of utilizing immersion within a liquid medium of enhanced quantum coherence to create a bio-communication pathway for observing and exploiting the biofield interactions of living organisms. The present disclosure provides an approach to biofield detection which embraces the idea that, as an energy field, the biofield interacts with matter and that nuclear resonance can be employed to detect its energetic signature around living systems. For those skilled in the art of conventional NMRI, one of the most striking aspects of the novel application described herein is that it does not seek to characterize the internal anatomical and metabolic features of the organism at all, but instead focuses on the resonance of the nuclei in the liquid medium surrounding the organism.

Successive measurements of biofield response to environmental factors of various living organisms and, in particular, humans, can then be characterized. Biofield effects can be isolated, identified, and catalogued. Therapeutic and treatment modalities utilizing the coherent fluid medium to form a bio-communication pathway can be evaluated and refined based upon application and repeated measurements.

Two emergent biofield patterns can be detected using the techniques described herein. The first pattern is a structured (layered) biofield pattern surrounding the living organism extending outward and generally conforming to the shape of the physical body. The second pattern is a localized anomalous pattern representing variations in the degree of phase coherence, and in many cases reflecting a diminishing of coherence in the endogenous biofield due to disease or disorder.

These biofield-related variations can be localized, isolated, and used as input to render images of the living organism's biofield in 2D and 3D. Over time, repeated measurements of the biofields of various living organisms and, in particular, humans can be characterized. Anomalies can be identified, catalogued, and classified along with known and probable underlying causes. Therapeutic modalities can be evaluated based upon application and repeated biofield measurements.

The systems and methods described herein can create a unified quantum coherent medium encompassing the living organism and the surrounding water volume, enabling the endogenous biofield to propagate outward and express exogenously within a highly resonate environment. NMRI can be used to extract and visualize this expression from the coherent medium. This medium is in essence a technology-enabled bio-communication pathway, and is bi-directional. The bi-directional communication presents the capability to pursue a number of research, medical diagnostic, treatment and therapeutic applications. These applications include the study and characterization of the time-dependent biofield effects of environmental agents such as EM fields and biotoxins, the classification of biofield signatures for pathogens and disease conditions, and the evaluation and development of treatment modalities including conventional western as well as Complementary and Alternative Medicine approaches.

The present disclosure describes the use of a NMRI apparatus including a main magnetic array, shims (or shim coils), magnetic gradient coils, and RF transmit and receive coils, that is specifically designed to excite, measure, and localize the transverse (spin-spin) relaxation of atomic species present within a fluid volume. The fluid volume can be contained within a specially designed fluid container suitable for use with the NMRI apparatus. A fluid management system can also be included.

The NMRI apparatus can include a computerized control system configured to control nuclear spin excitation and relaxation measurement of the fluid volume both with and without one or more living organisms present within the fluid volume. The magnetic resonance (MR) signals from each process can be detected, processed, and stored by the NMRI apparatus. The localized results of the two procedures are then compared and analyzed for biofield-related variations in relaxation time, rate and, potentially, other magnetic resonance MR signal characteristics.

These localized $T2^*$ response variations can be isolated and quantified to render an image of the biofield around the living organism. Colors can be assigned to variance range-value sets to reveal structural features and characteristics of the biofield.

Research and practical use of this apparatus and method can increase understanding of biofield characteristics and dynamics related to various living organisms, by relating biofield anomalies to known classification frameworks and potentially producing new categorization and classification schemes or adding to known classification schemes for healthy as well as disease and disorder conditions. This knowledge can further enable the development of integrated databases for diagnostics and treatment modality assessment.

FIGS. 1A and 1B illustrate, respectively, front and side views of a biofield detection system 100 configured to detect a biofield surrounding a living organism, such as a human being. The biofield detection system 100 can comprise, generally, a fluid container 102 and a Nuclear Magnetic Resonance Imaging (NMRI) system 104. The fluid container can generally be sized and configured to contain a fluid and a living organism to be evaluated. The embodiment shown in FIGS. 1A and 1B includes a cylindrical fluid container sized for evaluating adult humans, but fluid containers of other sizes can be implemented for smaller/larger living organisms.

As shown in FIGS. 1A-1B and 2A-2B, the fluid container 102 can comprise a transparent material such as acrylic glass (Poly Methyl Methacrylate). Transparent materials that do not contain ferromagnetic compounds, such as acrylics, can be advantageous since the gyromagnetic characteristics of the constituent bound atomic nuclei of acrylic materials do not impede or distort RF transmit and receive signals produced during biofield detection. For example, the chemical formulation of acrylic glass can enable clear differentiation in signal processing between fluid in the fluid container and the acrylic wall of the fluid container.

In the illustrative embodiment, a human subject is fully immersed in the fluid container 102. In one embodiment, the subject can be immersed standing upright in the fluid. In one specific embodiment, the container can be cylindrical in shape having dimensions of roughly 2-3 m in height, by 1-1.8 m in width, and a wall thickness of 1-2 cm. In other embodiments, the fluid container can be horizontally positioned to enable biofield detection while the human subject is in the prone position. In other embodiments, the fluid container can comprise various additional shapes. For example, the fluid container 102 can be rectangular in shape. For other types of living organisms, dimensional variations of rectangular, cylindrical, or spherical shapes may be used.

The fluid container can be filled with a fluid, such as water, having a temperature that is comfortable to the human subject (e.g., approximately room temperature water), but not of sufficient temperature to produce significant convective motion. In some embodiments, purified water can be used. Water can be desirable for use with the NMRI system due to its unique properties and the strong NMR response of the 1H nuclei. Other fluid mixtures containing a combination of water and other molecular compounds with suitable gyromagnetic ratios and/or paramagnetic ions can be used, such as $PO_4$. In some embodiments, the fluid container can be filled with a fluid from a fluid management system (described below) with a fluid specifically conditioned to maintain an enhanced-level of quantum coherence within the fluid volume.

In one embodiment, the fluid container can be accessed through an open top portion 108. The human subject can be lowered into the fluid through the top portion and stand upon or be supported by a platform 110 positioned near the bottom of the container. The platform 110 can comprise the same material as the fluid container, such as an acrylic glass. The fluid level in the fluid container and the platform height can be adjusted in accordance with the area of the biofield to be scanned. With full-body scans, the subject must be fully submerged in the fluid, with sufficient fluid coverage both above the head and below the feet of the subject. For example, the platform can be adjusted to provide at least 40 cm of fluid below the feet, and the container can be filled such that the level of the fluid is at least 40 cm above the head of the subject, ensuring the scan covers the biofield extending above the head and below the feet. For smaller scans of targeted body regions, it may not be necessary to fully submerge the subject. When the subject is fully submerged in the fluid, a breathing apparatus 112 such as a snorkel or breathable-air line can be used to allow the subject to breath.

Still referring to FIGS. 1A and 1B, the NMRI system 104 can be arranged adjacent to the fluid container 102 and can comprise an open bore assembly including a plurality of main magnets, shims (or shim coils), magnetic gradient coils, and RF coils (transmit and receive, phased-array, separate or combined). The main magnets used may include permanent, resistive, combined permanent and resistive, or superconducting. The NMRI system can be configured to generate a static magnetic field within the fluid volume of the fluid container.

Figure 3B:
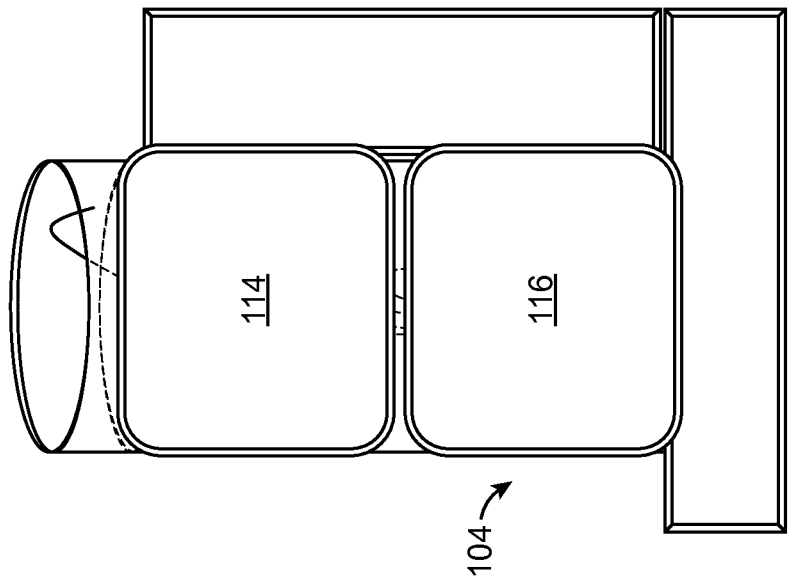
FIGS. 3A-3B show yet another embodiment of a biofield detection system.
Figure 3A:
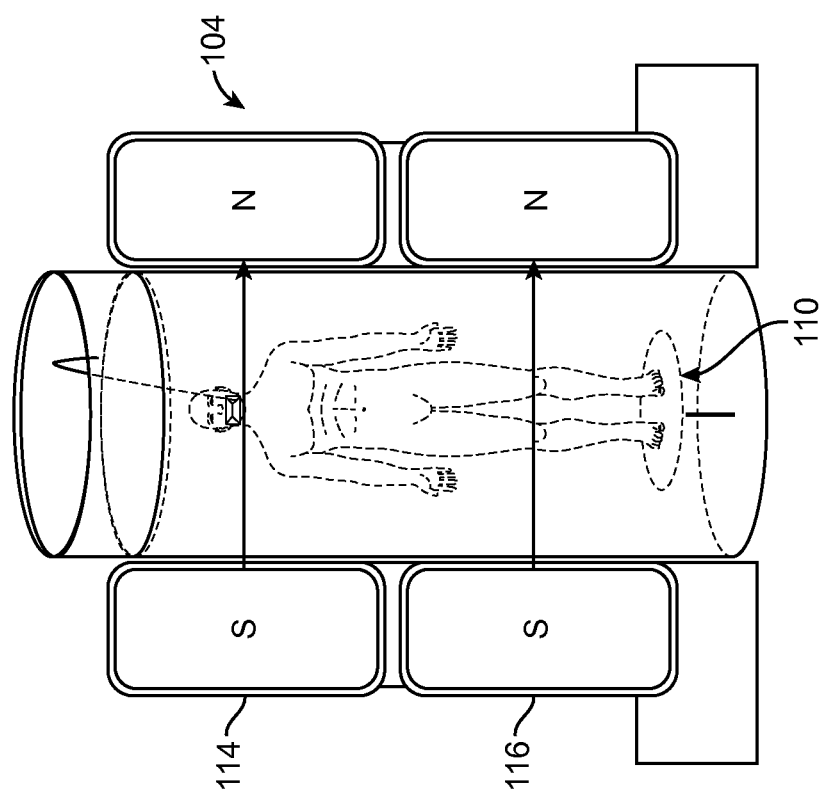

The embodiment of FIGS. 1A and 1B shows a NMRI system comprising a single pole-pair 114, having a "south pole" S and a "north pole" N. However, the embodiment of FIGS. 3A and 3B shows a NMRI system 104 having two pole-pairs 114 and 116, having a pair of "south poles" S and a pair of "north poles" N. The pole-pairs of the NMRI system 104 can be supported by a frame 117. In some embodiments, the frame 117 can be configured to allow for rotation and/or movement of the NMRI system to accommodate both vertically arranged and horizontally arranged fluid containers. For example, the frame 117 can include one or more hinges, rails, and/or tracks to allow the pole-pairs to be rotated and moved into the proper imaging position. In some embodiments, the frame can further include a hydraulic system configured to move and rotate the NMRI system.

The dimensions of the fluid container and NMRI system can vary based upon the types of organisms to be evaluated. For smaller organisms, the dimensions of the fluid container can allow for conventional NMRI system configurations to be employed. Larger organisms, and therefore larger fluid containers, may require modified NMRI system configurations. For example, a fluid container designed for human subjects may need to accommodate a vertical standing position in addition to a horizontal prone position. To accommodate both positions, the NMRI system can include a frame configured to be rotated and elevated so as to position magnetic poles at either side of the human subject within the fluid container. In order to provide maximum flexibility for handling both vertical and horizontally-aligned scan sequences, the pole-pair configuration of the NMRI system can be designed to rotate between multiple positions. In some embodiments, the fluid container is emptied during this rotation process to minimize the stress loads involved this operation.

Various NMRI configurations can be implemented, including a di-pole open-bore configuration, a 'C'-shape open-bore configuration, or a closed-bore configuration. Fully closed-bore designs for human subjects may be less desirable due to the potential for inducing claustrophobia.

In the case of human subjects, it can be desirable to view the biofield as an integrated whole rather than simply a portion of it. Due to magnetic gradient non-linearity (i.e., the tendency of a magnetic field to degrade as a function of distance from the magnetic isocenter), it may not feasible to get a full body picture of the adult human biofield using a single magnetic pole-pair since the biofield extends above the head and below the feet of the subject. Therefore, some full body scans of human subjects may require a special configuration of magnetic assemblies involving two pole-pairs, as shown in the embodiment of FIGS. 3A and 3B. In other embodiments, more than two pole-pairs can be included in the NMRI system depending on the size of the subject to be imaged.

In conventional NMRI systems designed for use on humans and animals, RF receive coils are typically designed for the specific anatomical features to be scanned (e.g., brain, upper thorax, legs, etc.), and are often placed directly on the body in advance of the scan sequence. However, according to the present disclosure, the NMRI system is configured to image the biofield surrounding the subject, but not the subject itself, by detecting transverse (spin-spin) relaxation of excited atomic nuclei within a fluid volume surrounding the body, and not inside the body. Therefore the receive coil architecture of the present disclosure can be a uniform, multi-channel phased array configuration which is adapted to support parallel imaging of the fluid volume surrounding the subject. As will be described in more detail below, the coil array is the inner-most element of the magnetic pole assembly, and interfaces with the outside wall of the fluid container.

Water is highly interactive with its surrounding environment, engaging in electrostatic interactions with other dipoles and ions and rapidly forming hydrogen bonds, as both donor and acceptor, with other water molecules and molecular compounds dissolved in water. The hydrogen bonding characteristic of the water molecule gives it enormous morphological flexibility. External magnetic fields increase the stability and hydrogen bond strength of supra-molecular water clusters while decreasing the self-diffusion of individual water molecules. Exposure to magnetic fields can promote formation of both linear and closed chains of hydrogen-bonded water clusters. The present disclosure draws upon both the field of (NMRI) and quantum electrodynamics derived from theoretical research and experimental evidence related to the phenomenon of quantum coherence in condensed matter.

The biofield detection system configurations described herein create a medium in which the subject, as a quantum coherent system, is immersed within a fluid volume that can be enhanced to optimize its coherence properties. Coherence can be enhanced in a fluid volume exposed to the static magnetic field of a NMRI system by the introduction of trace amounts of extended coherence-facilitating non-aqueous compounds. The systems and methods described herein enable coherent interplay between the matter fields and interference patterns of the fluid volume and living organisms in which phase information is readily exchanged. Bio-information communicated from the subject into the fluid volume changes the phase and structure (imprinting) of the quantum coherence domains therein. These biofield induced changes in the fluid volume represent either a greater or lesser degree of coherence (and thus structure) from that of the fluid volume, absent the living organism. Because the degree of structure in the fluid volume equates to a corresponding increase or decrease in bonding, this will be reflected in measured NMR signatures (T2* transverse relaxation times) of the fluid volume.

Figure 4:
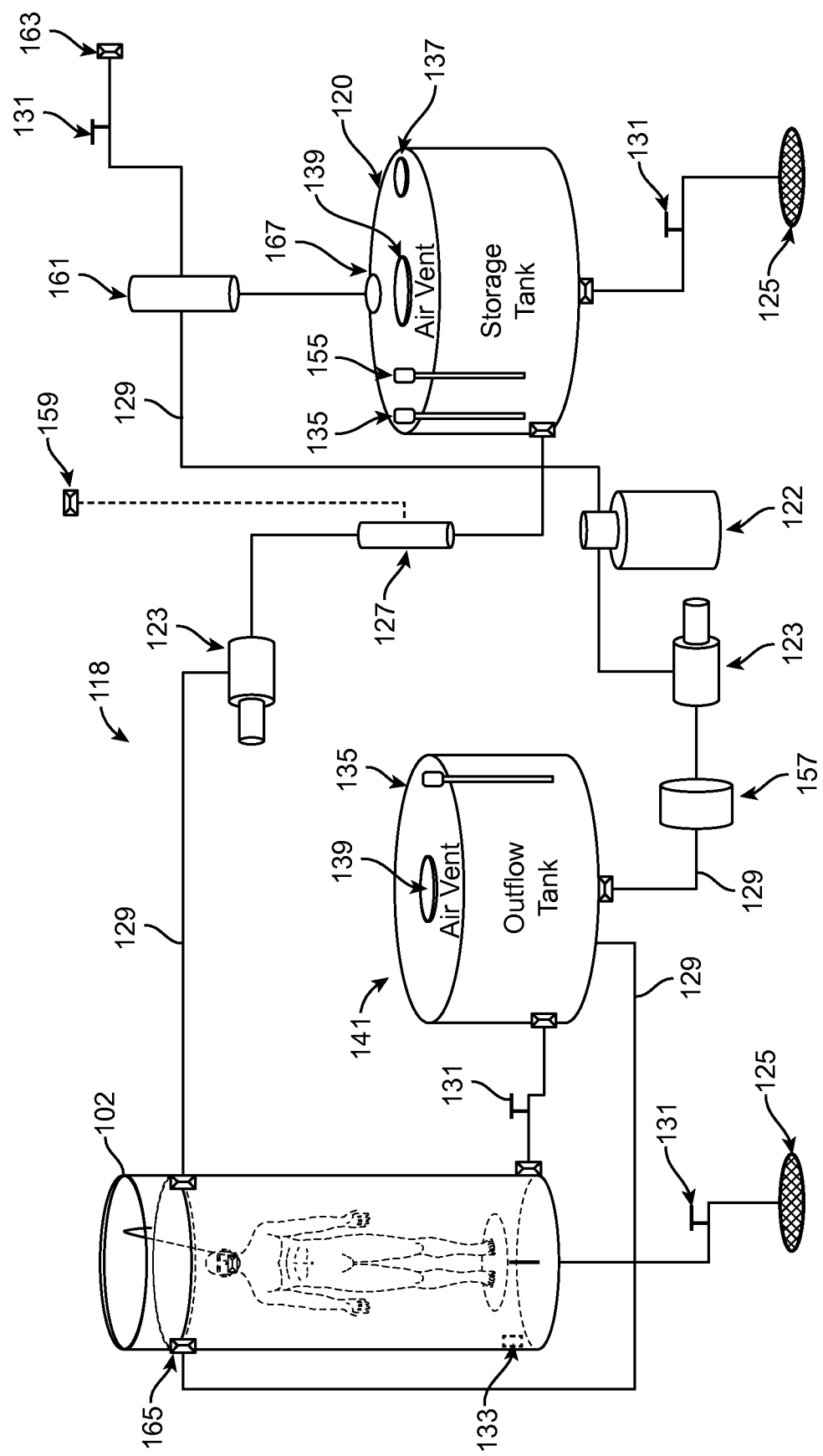
FIG. 4 illustrates a fluid management system of a biofield detection system, including a storage tank and a fluid management system.

Referring now to FIG. 4, the biofield detection system 100 can further comprise a fluid management system 118 that includes a storage tank 120, a filtration system 122, one or more pumps 123 configured to pump fluid from the storage tank 120 into and out of the fluid container 102 via lines 129 and valves 131. The pumps 123 can optionally pump fluid out of the fluid container into one or more drains 125 and/or the storage tank 120 or outflow tank 141, and can also be configured to maintain the fluid level in the fluid container 102. Fluid in the fluid container can be rapidly drained to drain 125 through a valve 131 in the event that the fluid volume is contaminated or needs to be drained quickly. The storage tank 120 can be sized and configured to hold a large enough volume of fluid to fill the fluid container 102 during or prior to biofield detection. In some embodiments, the storage tank can hold enough fluid to fill the fluid container several times over.

The fluid management system 118 can further comprise a temperature control system 127 configured to control the temperature of the fluid as it is delivered to the fluid container, including either heating or cooling the fluid. The temperature control system can be powered by, for example, a natural gas source 159.

Additional features can be included in the fluid management system, such as a temperature sensor 133 in the fluid container, a level sensor 135 in the storage tank and outflow tanks, a PH sensor 155 in the storage tank, an access cap 137 in the storage tank for visual inspection of the storage tank, and air vents 139 in the storage and outflow tanks for venting the tanks. The fluid container 102 can optionally include an overflow outlet 165 to prevent the container from being overfilled with fluid.

Referring still to FIG. 4, water can be introduced into the system from water source 163 which may be tap water or a rainwater-capture cistern. These sources typically contain solutes that may encourage the formation of coherent domains within the water volume. The valve 131 can be controllable from a system control console or, alternatively, may be manually controlled.

Input water can be funneled through a water conditioning unit 161. This water conditioning unit can be any water conditioning unit known in the art, such as an acrylic glass cylinder filled with glass or quartz crystal spheres, and can be positioned vertically above the storage inlet 167. The water can be allowed to percolate from the top down of the water conditioning unit and into the storage tank 120. In some embodiments, the water conditioning unit may also contain solid tablets of non-aqueous compounds, such as NaCl or KCl. This enables the water conditioning unit of the fluid management system to add trace amounts of non-aqueous compounds to the water as it is introduced into the fluid management system. This water conditioning unit is designed to promote the formation of coherent domains, thereby enhancing the coherence of the fluid delivered to the fluid container.

Fluid in the fluid management system can be recycled by emptying the fluid volume from the fluid container into the outflow tank 141 through valve 131. The fluid can be pumped from the outflow tank through demagnetizer unit 157 to effectively de-structure the water and thereby remove the EMF/bio-information imprinting contained within the water coherent domains. The de-imprinted water can flow through filtration system 122 which can contain levels of various materials that may include gravel, sand, and/or charcoal to filter and/or purify the fluid. The filtered fluid can be pumped back into the water conditioning unit 161 with pump(s) 123, where it can be re-conditioned and transferred into the storage tank.

Figure 5:
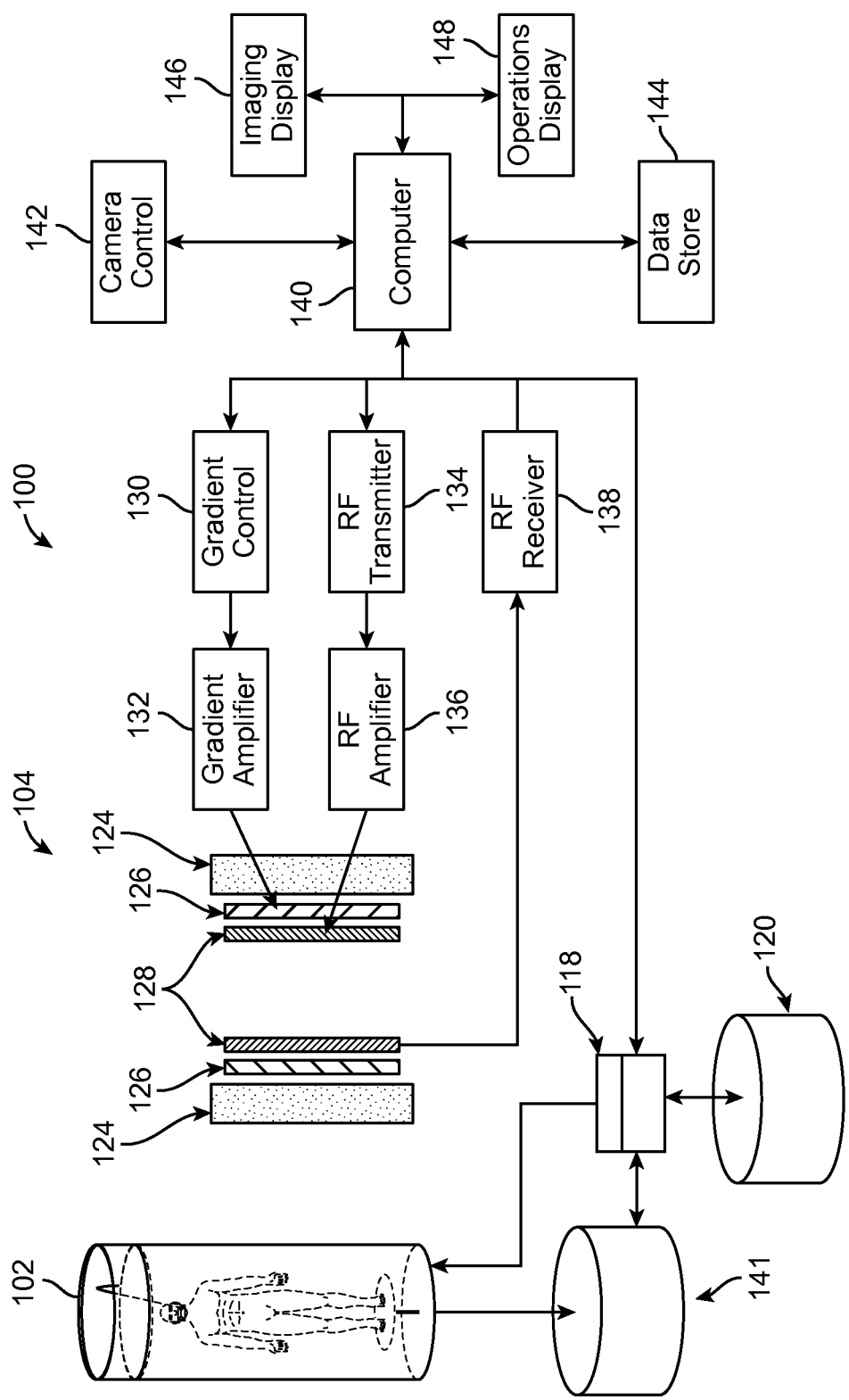
FIG. 5 is a schematic diagram of a biofield detection system.

FIG. 5 is a schematic diagram illustrating additional details of the biofield detection system 100, including fluid container 102, NMRI system 104, fluid management system 118, storage tank 120, and overflow tank 141. The NMRI system 104 can include a plurality of main magnets 124, gradient coils 126, and RF coils 128. The gradient coils 126 can be controlled by a gradient control 130 which produces gradient waveforms that can be fed through a gradient amplifier 132 to vary the magnetic field linearly across the imaging volume. The RF coils 128 can be controlled by a RF transmitter 134 which produces RF waveforms that can be fed through an RF amplifier 136 to excite the nuclei within the imaging target volume and detect the resulting nuclear magnetic resonance signal at RF receiver 138.

Overall control of the biofield detection system 100 can be handled by computing system or computer 140. The computer 140 can be a remote computer system configured to control all aspects of the biofield detection system 100, including control of the NMRI system and all imaging pulse sequences, and control of the fluid management system 118 including fluid management of the fluid container 102. The computer 140 can include hardware and software configured to control every aspect of the NMRI system, including executing the specific imaging algorithms and pulse sequences necessary to produce NMR imaging. The computer 140 can further run image processing software configured to manipulate, enhance, and display biofield images resulting from the NMR imaging process on imaging display 146.

The computer 140 can be located in a control room of the imaging facility, enabling operators to monitor and initiate control actions from that location. In some embodiments, the computer 140 can be operatively coupled (e.g., direct electrical connection, or a wireless connection such as WiFi, Bluetooth, cellular, etc.) to the NMRI system and/or the fluid management system 118. In some embodiments, a wireless connection between the computer and the NMRI system may introduce undesirable environmental electromagnetic fields, and thus a direct electrical connection may be preferred. This configuration enables imaging control, fluid level control, as well as the ability to empty the fluid container and maintain desired water conditions between uses, or in the case of an alternative embodiment, to reposition the fluid container in the horizontal position in order to scan the human subject in the prone position.

One or more cameras can be located on or near the biofield detection system to record the overall process of biofield detection. The camera(s) may also provide remote supervision or observation of the biofield detection. In some embodiments, the computer 140 can further be configured to provide camera control 142 of any cameras on, in, or near the biofield detection system 100, can provide data storage 144 for all the data gathered during biofield detection, can provide imaging display 146 of the NMR images, and operations display 148 relating to any and all operating parameters of the system during use. The imaging display 146 can be a high-resolution graphical display adapted to provide visualization and manipulation of the images generated by the biofield detection system in black and white and/or full color, including 2D and/or 3D views. The graphical and operations displays can include an input device, such as a mouse, keyboard, trackpad, and/or graphical user interface (GUI) such as a touchscreen to allow a user to interact with the computer 140 to initiate and manage the biofield imaging process, fluid management, monitoring of the status of various sensors, and generation and/or manipulation of images generated during the process.

As described above, the biofield detection system of this disclosure is configured to detect a biofield surrounding a living organism, and more specifically, to detect the biofield in a fluid surrounding the living organism's body. According to one embodiment, one technique for detecting a biofield involves first obtaining a baseline scan sequence of the fluid volume with the NMRI system without the presence of a living organism, then obtaining a second scan with the living organism positioned in the fluid volume. The systems and methods for detecting a biofield described below will be made with reference to FIGS. 5 and 6.

Baseline Scan Sequence:

The objective of the baseline scan sequence is to establish a map of the inherent magnetic field inhomogeneity and diffusion characteristics of the fluid volume (e.g., the fluid in the fluid container 102) in the absence of a living organism. For a human subject, a target scan area of the body is pre-determined and then, based upon the patient's height and weight, a target area of the fluid volume within the fluid container is derived. The operator can set the fluid level in the fluid container with computer 140 and fluid management system 118 to ensure that the baseline scan will produce a map of the target area consistent with the area of the subject to be scanned during the subsequent detection scan sequence. For example, if a full body scan of the human subject is to be performed, the operator can fill the fluid container to a level that ensures fluid will extend a sufficient distance above the head and below the feet of the subject.

In some embodiments, the fluid volume can be treated with the fluid management system to increase a coherence of the fluid volume and create an optimal environment or bio-communication pathway for observing, studying, and accessing bi-direction interactions. Increasing the coherence of the fluid volume, such as by adding trace amounts of non-aqueous compounds to the fluid with the fluid management system as described above, can enhance the ability of the NMRI system to detect biofield information from the living organism. Enhancement of the fluid volume further enables detection and characterization of the biofield emitted from living organisms, of the effects of environmental agents on the biofield, and of the efficacy of treatment and therapeutic modalities, and further enables the development of new and enhanced modalities.

First, the operator can select the scan protocol to be used during the baseline scan. The protocol alternatives for biofield detection are more limited than conventional medical NMRI techniques, since the target of the biofield scan is the fluid volume within fluid container 102 that does not contain any of the structure or complexity of the internal human anatomy. In one embodiment, a variation of the "Spin-Echo" pulse sequence can be used to substantially mitigate local magnetic field inhomogeneity as well as diffusion and spatial distortion effects in the fluid volume.

Prior to running the baseline scan, the operator may also initiate localizer and/or calibration scans. The resulting information can be used to refine the scan plot including field of view, direction of location encoding, slice thickness, voxel (spatial) dimension, and parallel imaging method.

Figure 6:
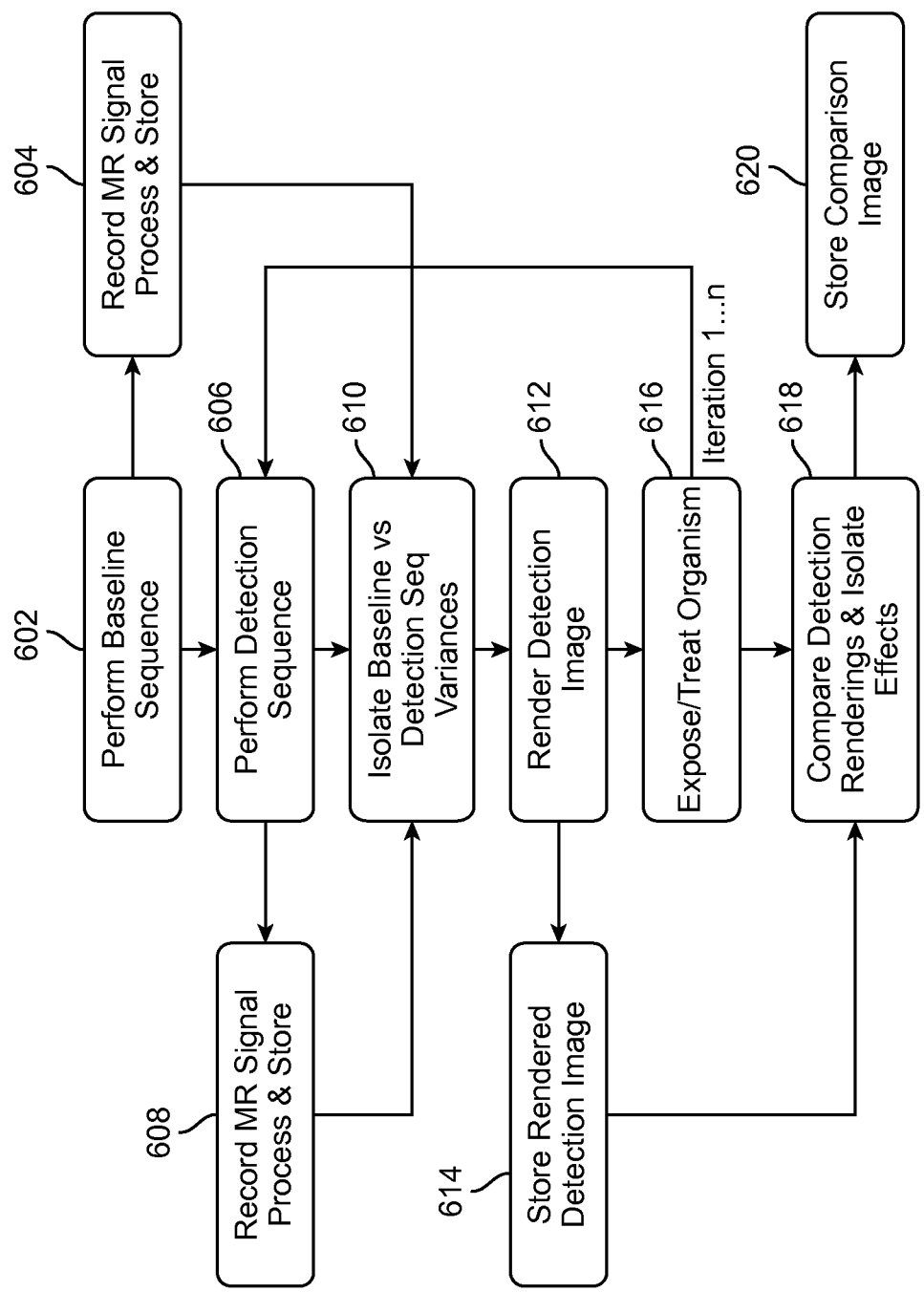
FIG. 6 is a flowchart describing a method of rendering a biofield image.

Referring to step 602 of FIG. 6, the operator can perform the baseline scan with the NMRI system. The baseline scan can begin with an automated pre-scan. This process may include coil turning and matching, transmit and receive gain adjustment, and dummy cycles. The baseline scan sequence can be executed against the target fluid volume within the fluid container. This baseline scan can include the transmission of the specified RF excitation pulse sequences with the RF transmit coils and the imposition of spatial encoding upon the main magnetic field with the gradient coils, described and shown in FIG. 5. In some embodiments, a parallel imaging (PI) technique can be employed to reduce total imaging cycle time.

The magnetic resonance signals produced by the transverse (spin-spin) relaxation of 1H nuclei within the target fluid volume can be detected by the RF receive coil array, amplified, digitized, processed using 2D and/or 3D fourier transformation, and recorded and/or stored as a baseline dataset at step 604 of FIG. 6 by the biofield detection system (such as by computer 140 with data storage 144 in FIG. 5). The baseline dataset can be processed to include digitized, spatially-encoded, quantitative values for T2* transverse (spin-spin) relaxation times in the fluid volume.

Detection Scan Sequence

Next, the target subject, such as a human subject, can be positioned on the platform within the fluid container. The human subject can be scanned while wearing clothing such as swimwear, or can be scanned without any clothing at all. Depending upon the area to be scanned, the subject's head may be above or below the water line. A breathing apparatus as described above can be utilized if the subject's head is to be below the water line during the scan process, such as during a full body scan. The target subject can be positioned slowly within the fluid container to minimize the diffusion resulting from fluid currents within the container. Before initiating the detection scan sequence, the subject can be given time to remain still within the fluid container to allow fluid currents to settle. During this time the operator performs the calibration sequence and confirms the scan plot relative to the subject body position, and adjustments are made if needed.

Next, the detection scan sequence can be initiated at step 606 of FIG. 6, which includes the same pulse sequence as used above in the baseline scan, and the resulting MR signal is again detected, amplified, digitized, processed and stored as a detection dataset at step 608 of FIG. 6 with the biofield detection system. The detection dataset includes digitized, spatially-encoded, quantitative values for T2* transverse (spin-spin) relaxation times in the fluid volume when the subject is positioned inside the fluid volume.

Next, referring to step 610 of FIG. 6, the stored data from the prior baseline and detection scans can be retrieved and compared to isolate the baseline vs. detection scan variances. The two datasets can be compared and analyzed at the voxel- and/or pixel-level by the computer 140 of the biofield detection system to identify and isolate discrete variations in observed transverse (spin-spin) relaxation time (T2*) and/or relaxation rate (R2*). As described above, both the baseline dataset and the detection dataset include digitized, spatially-encoded, quantitative values for T2* transverse (spin-spin) relaxation times in the fluid volume. However, the baseline dataset is based on the NMR properties of the fluid volume without a subject, and the detection dataset is based on the NMR properties of the fluid volume with a subject positioned in the fluid volume. The spatially-encoded data from the baseline and detection datasets can be compared to produce a biofield dataset that includes the variances (voxel and pixel-level) in the T2* times between the baseline and detection datasets.

Image Rendering

The localized variations between the baseline and detection datasets from step 610 can then be used to render a biofield image of the biofield surrounding the subject at step 612 of FIG. 6. The rendered image(s) can be stored at step 614 of FIG. 6. The biofield image can be further enhanced or visualized by assigning colors, intensities, contrast, or other image processing techniques to variation range-value sets and performing volume rendering. In some embodiments, the biofield image can show two emergent patterns. The first can be a structured (layered) biofield pattern surrounding the subject and extending outward and generally conforming to the shape of the subject's body. The second can be localized anomalous patterns representing variations in the degree of phase coherence, and in many cases reflecting a diminishing of coherence in the endogenous biofield due to disease or disorder in the subject. Since disruptions of coherence within living tissues is often a precursor to disease, the condition may not yet be physically manifest, but can be identified in the biofield image.

Rendered biofield scan images can be viewed and manipulated by the user from both 2D and 3D perspectives. 2D scans can be displayed by clicking on a body icon at the desired body height to show the biofield scan slice at that location. The user can then scroll through consecutive scan slice images starting from that location. In the 3D perspective, the user can rotate the inward-facing viewpoint to any position on a logical sphere enclosing the full biofield image. Furthermore, the user can zoom-in and -out from any viewpoint along the logical sphere. The user can monitor and control the zoom based upon depth from the outer edge of the logical sphere. Layers or characteristics of the biofield image can be removed or isolated by selection of range-value sets. In some embodiments, predefined viewpoint positions can be automatically programmed into the visualization system, and the user can easily select any of these viewpoint positions with the click of a button. For example, predefined viewpoint positions such as anterior, posterior, and lateral views, and a viewpoint from the edge of the logical sphere can be implemented into the system. The user(s) may also define their own predefined viewpoint positions which can then be made selectable.

Users of the system may assign colors from a color pallet to specific range-values of detection signal variance, thereby creating user-defined biofield color schemes to be used in the NMRI image rendering process. In other embodiments, users may select from pre-packaged or user-defined color schemes when viewing biofield images to create uniformity in the rendered biofield images. Similarly, pre-defined or user customizable contrast schemes using gray-scale colorization can enable users to highlight anomalies in the biofield image such inconsistencies in structure, intensity and form.

During this rendering process, the human form itself can be displayed as a surface rendering largely because the receive coil array is not designed to detect specific internal anatomical detail within the body, and any such available MR signals may not be of particular use in the biofield detection application. Termination of rendering at the surface of the body also serves to reduce the overall biofield image rendering cycle time.

Figure 7A:
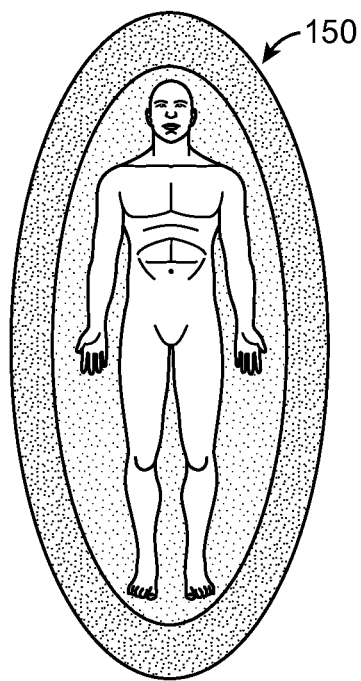
Figure 7B:
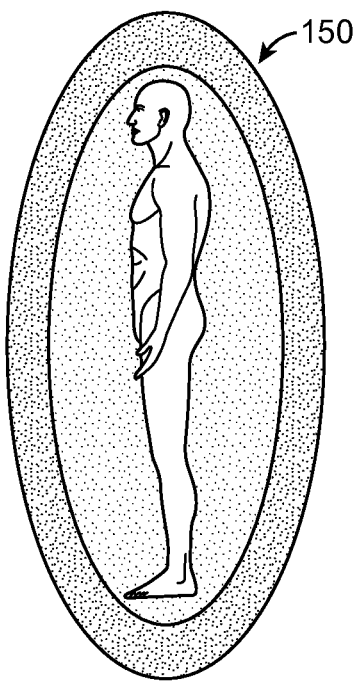

The biofield of the subject can extend out 40-80 cm from the subject's body and, depending upon the rendering technique used, can be visualized as a translucent multi-layered field of energetic radiation. One example of how a biofield 150 can be visualized is shown in a front view in FIG. 7A, in a side view in FIG. 7B, and in a top-down view in FIG. 7C.

Figure 7C:
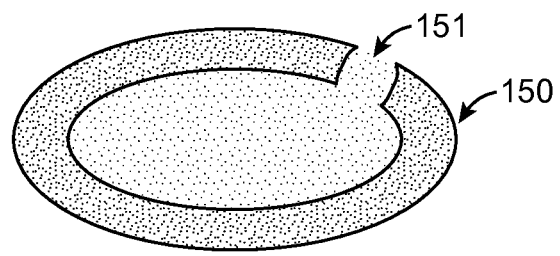

The rendered biofield image can then be displayed and manipulated by the operator in 3D and/or 2D, by rotating, zooming, and manipulating the view perspective. Non-uniformities or anomalies in the biofield can be visible in the rendered biofield image, and can be further explored and clarified by introducing image contrast techniques, selecting for specific patterns, or range-value sets. For example, FIG. 7C shows a top-down view of a subject's biofield 150, including an anomaly or non-uniformity 151. In some embodiments, the computer of the biofield detection system can perform these enhancements automatically. Selected perspectives of the biofield can be captured as still images and/or movies, which can be stored by the computer 140 in data storage 144.

Exposure/Treatment Phase

Next, at step 616 of FIG. 6, the living organism and/or the fluid volume within the fluid container can be exposed to specific environmental factors. For example, in some embodiments, one or more environmental factors can be introduced to the living organism or the fluid volume. Introducing environmental factors into the fluid volume, or on, in, or near the living organism can allow for the study and observation of complex bi-directional interactions of biofields emitted from the living organism and interacting with its environment and/or the introduced environmental factor(s). Introduction of environmental factors can include the following:

Man-made Electromagnetic Fields: EMF sources (e.g., visible, infrared light) can be directed at specific locations on the body or in proximity to the body from positions inside or outside of the fluid container, other sources of electromagnetic radiation such as microwave radiation (mobile devices) may be placed in sealed containers and positioned within the fluid container at various distances from the body, held in-hand, or attached to the body of the subject. Electromagnetic sources may also be positioned outside of the fluid container.

Naturally-Occurring Electromagnetic Fields: EMF sources (e.g. sunlight) can be directed at specific locations on the body or in proximity to the body from positions inside or outside of the fluid container.

Medical and/or Therapeutic Treatment Modalities: this may involve discrete or combined use of chemical compounds used in western medicine including gas, aerosol, liquid or solid forms addressed in part under non-living matter. It may also involve other Complimentary Alternative Medical (CAM) modalities such as: Whole Medicine Systems—Acupuncture, Naturopathic Medicine, Homeopathy, Ayurveda, Herbalism; Mind-Body Medicine—Meditation, Reflexology, Qi Gong, Vipassana, Yoga, Tai Chi, Breathing, Prayer, Biofeedback, Hypnosis; Body-Based Practices & Energy Medicine—Osteopathic/Chiropractic Care, Massage, Myofacial Release, Cranio-Sacral Therapy, Healing Touch, Reiki, Crystal Therapy; and/or Biologically-Based Interventions—Botanical Medicine, Oil Extracts, Probiotics, Clinical Nutrition Therapy Chemical compounds, minerals, loose materials, fabrics: can be placed into sealed containers and positioned within the fluid container at various distances from the body, held in-hand, or attached to the body of the subject. In some embodiments, these materials are not allowed to directly interact with the fluid volume so as to mitigate the potential effects of chemical exchange in the NMRI process.

Rocks and crystals: can be placed within the fluid container at various distances from the body, held in-hand, or attached to the body of the subject.

Foods: can be ingested by the subject, placed into sealed containers and positioned within the fluid container at various distances from the body, held in-hand, or attached to the body of the subject.

Medications, supplements: can be ingested or inhaled by the subject, or topically-applied, or injected into the body by an attendant physician.

Aerosols: may be inhaled by the subject or placed into sealed containers and positioned within the fluid container at various distances from the body, held in-hand, or attached to the body of the subject Subsequent Detection Scan Sequences After the living organism and/or the fluid volume within the fluid container has been exposed to specific environmental factors one or more subsequent detection scan sequences can be initiated again at step 606 of FIG. 6. The subsequent detection scan sequence(s) can utilize the same pulse sequence as in the first detection scan, and the resulting MR signal can again be detected, amplified, digitized, processed and stored as subsequent detection dataset(s) at step 608 of FIG. 6 with the biofield detection system. The subsequent detection dataset(s) can include digitized, spatially-encoded, quantitative values for T2* transverse (spin-spin) relaxation times in the fluid volume when the subject is positioned inside the fluid volume. The subsequent detection datasets can again be retrieved and compared to isolate the baseline vs. detection scan variances at step 610 of FIG. 6, as described above. Additional detection images based on the subsequent detection scans can be rendered at step 612, and stored again at step 614 of FIG. 6.

Due to the introduction of environmental factors into the fluid and/or living organism, the time-delay relative to the initiation of the subsequent detection scan sequences can be varied as bio-effects may vary as a function of exposure time. During this time-delay, the subject can remain still within the fluid container to minimize the effects of diffusion from circulating currents in the fluid volume. In some embodiments, the water volume can be drained, optionally demagnetized, and refilled to refresh and dissipate the potential effects of water imprinting (water memory) from the previous detection scan sequences. At the appropriate time, the operator can perform a calibration sequence and confirm the scan plot relative to the subject body position, and adjustments can be made if needed.

Biofield Image Comparison:

The rendered images from the baseline, detection, and successive, post-exposure/treatment detection scan sequences can then be retrieved and visually compared side by side at step 618 of FIG. 6. Automated computerized algorithms can be configured to detect and highlight biofield variances (changes in spatially-encoded T2* transverse relaxation) between successive detection scans. These before-after variances can then be quantified, highlighted and stored by the system at step 620 of FIG. 6.

The computing system described above can be configured to execute software or software algorithms to perform many of the method steps above, including performing the baseline scan at step 602, recording and storing the baseline dataset at step 604, performing the detection scan at step 606, recording and storing the detection dataset at step 608, comparing the baseline and detection scans at step 610, rendering a biofield image at step 612, storing the rendered image at step 614, exposing the organism and/or fluid volume to environmental factors at step 616, comparing the baseline, detection, and post-exposure scans at step 618, and storing the before-after variances at step 620. The computing system can also be configured to display the rendered biofield images to the user or operator.

Figure 8B:
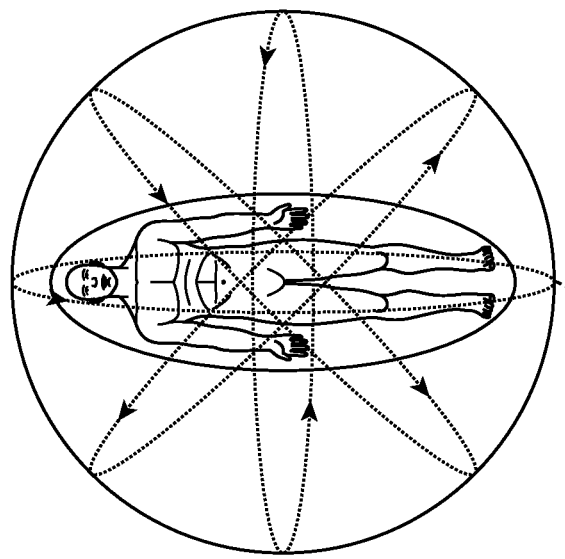
FIGS. 8A-8C show one embodiment of what image visualization and comparison may look like after comparing baseline, detection, and subsequent detection scan sequences.
Figure 8C:
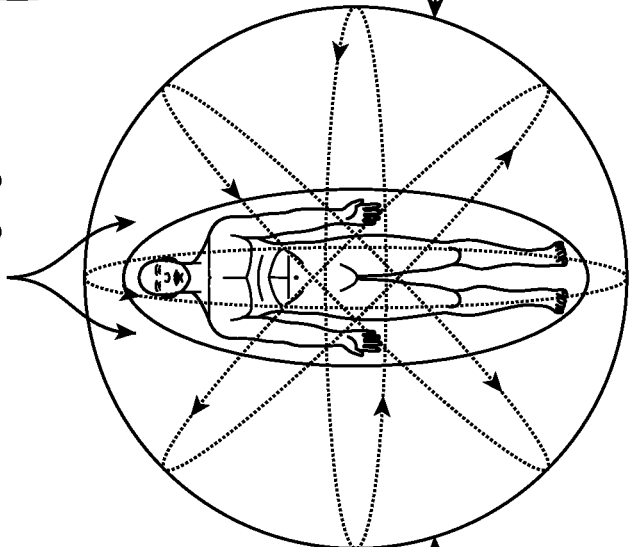
Figure 8A:
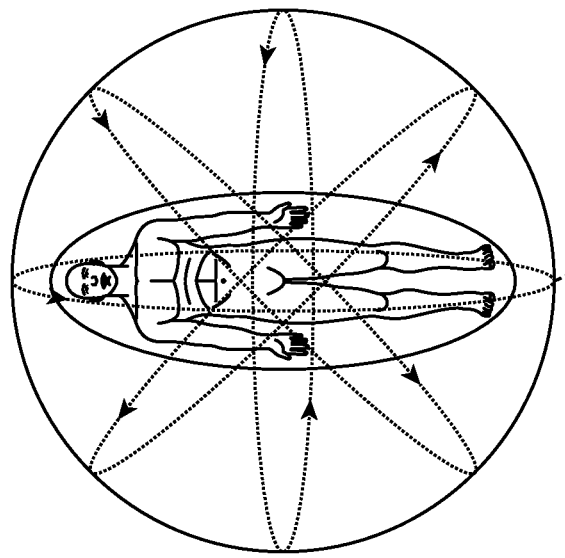

FIGS. 8A-8C show what image visualization and comparison may look like after comparing the baseline, detection, and subsequent detection scan sequences described above with respect to FIG. 6. The initial detection and successive detection sequences can be viewed and visually compared side by side, as shown in FIGS. 8A and 8B.

A hybrid comparison image between the detection scans, and quantitative analysis can also be derived at this point, as shown in FIG. 8C. A computerized algorithm can be configured to retrieve and compare the data files used to render the detection scan and successive detection scan images. These data files contain values representing variances (from the Baseline scan) in the spatially-encoded T2* transverse relaxation times of the 1H nuclei within the fluid volume. The computer algorithm can then compare the variances recorded in the detection scan files and successive post-exposure detection scan files voxel by voxel, pixel by pixel, identifying and quantifying variances of significance and writing those to a new, 'Comparison', file. The comparison sensitivity can be parameterized and easily modified.

The resulting comparison file can then be used to render an image that can be over-laid on the post-exposure/treatment image or viewed independently—showing only the areas of the biofield that experienced changes between the initial detection scan and successive detection scans.

Colorized contrast schemes can be utilized in which colors are assigned to variance range value-sets, the changes can be visually depicted as either diminishing or enhancing the vitality of the biofield. For example, gray-scale colorization enables users to highlight anomalies in the biofield image such inconsistencies in structure, intensity and form. Bright and vibrant colors may be used to highlight constructive improvements to the biofield.

In the case of long-term studies or therapeutic treatment programs, repeated measurements and the associated stored biofield data files and renderings can be analyzed and compared to create a visual and quantitative time-series of biofield changes.

The biofield dataset(s) and or biofield image(s) generated by the systems and methods of this disclosure can be used to detect, identify, classify, and/or catalogue the endogenous injury, tissue damage, disease, infection, and neurological, physiological, and psychological disorders of the living organism that is imaged. Each condition, depending upon a number of factors including its development stage and the overall health and vitality of the organism, will present itself as an anomalous pattern in the biofield image. These patterns may be localized to specific areas of the anatomy, have varying degrees of definition, shape and clarity, and extend to varying distances within the biofield.

Identifying and cataloguing the underlying conditions associated with a given biofield anomaly can be accomplished initially by associating anomalous biofield patterns with conditions identified using other conventional diagnostic techniques. For example, for a given human subject Polycystic Kidney Disease (PKD) may have been previously diagnosed using ultrasound. The biofield image can show an anomalous pattern originating near the affected kidney. Based upon the prior positive diagnosis, this pattern can be identified and catalogued as high probability PKD, and be related to a known classification framework and classified as both a Genetic and Kidney Disease. Repeated periodic measurements may provide an understanding of the biofield pattern of PKD disease progression. The PKD pattern may be distinct from other kidney diseases, or may be similar to others such as Renal Cell Cancer. Over time both the similarities and distinctions can be more precisely understood and catalogued. Therefore, biofield patterns can be associated with known prior diagnostics.

The biofield detection system described herein can further include machine learning diagnostic integration which enables the system to identify potential disease, infection, physiological or psychological conditions associated with anomalies detected within the biofield image. The machine learning algorithms can draw from a library of biofield images and associated underlying causal conditions. This library can also be made available to users as a heuristic tool for assessing biofield anomalies and their probable causes. The biofield detection system can integrate a cataloguing and classification system, such as the internationally recognized classification framework ICD-10, to support manual diagnosis, as well as automated pattern recognition and machine learning diagnostic algorithms. Beyond the use of prior diagnostics, is the opportunity to establish a development pattern for diseases and disorders that extends beyond the physical manifestation of the disease within the body. Because the energetic signature of disease may project into the biofield before it is physically manifest in the body and linger after it has healed or gone dormant, biofield detection using the systems and methods described herein can provide the opportunity for development of an extended characterization and recognition of lifecycle progression for disease. With such a diagnostic capability, biofield detection and imaging becomes more than an adjunct to other conventional diagnostic techniques, it becomes a method with potentially superior diagnostic reach.

A method of imaging a biofield surrounding a living subject is provided, comprising the steps of scanning a fluid volume with a nuclear magnetic resonance imaging system to produce a baseline dataset, scanning the fluid volume with the nuclear magnetic resonance imaging system while the living subject is disposed within the fluid volume to produce a detection dataset, comparing the detection dataset to the baseline dataset with a computing system to produce a biofield dataset that includes spatially-encoded, discrete variations in observed transverse relaxation time and/or relaxation rate in the fluid volume, and generating, with the computing system, an image of the biofield surrounding the living subject from the biofield dataset.

In some embodiments, the method further comprises identifying biofield anomalies from the image for diagnostic purposes. In other embodiments, the method further comprises cataloguing biofield anomalies from the image for diagnostic purposes. In additional embodiments, the method further comprises relating biofield anomalies from the image to known classifications for diagnostic purposes.

In some embodiments, the method further comprises identifying a disease in the living subject based on the image. In other embodiments, the method further comprises identifying an infection in the living subject based on the image. In alternative embodiments, the method further comprises identifying a physiological condition in the living subject based on the image. In additional embodiments, the method further comprises identifying a psychological condition in the living subject based on the image.

In one embodiment, the living subject comprises a human subject.

In some embodiments, the method further comprises introducing one or more environmental factors into the fluid volume, scanning the fluid volume with the nuclear magnetic resonance imaging system while the living subject is disposed within the fluid volume to produce a second detection dataset, comparing the baseline dataset to the second detection dataset with the computing system to produce a second biofield dataset that includes discrete variations in observed transverse relaxation time and/or relaxation rate in the fluid volume, and generating, with the computing system, a post-exposure image of the biofield surrounding the living subject from the biofield dataset.

In some embodiments, the method further comprises comparing the post-exposure image to the image to detect biofield variances before and after the introduction of the one or more environmental factors into the fluid volume.

In one embodiment, the one or more environmental factors are selected from the group consisting of man-made electromagnetic fields, naturally occurring electromagnetic fields, gases, liquids, aerosols, solids, chemical compounds, minerals, fabrics, crystals, foods, and medications. In other embodiments, the one or more environmental factors comprises a therapeutic and treatment modality.

In some embodiments, the method further comprises treating the fluid volume to increase a coherence of the fluid volume.

In additional embodiments, the method further comprises demagnetizing the fluid volume before scanning the fluid volume to produce the second detection dataset. In some embodiments, the method comprises demagnetizing the fluid volume before scanning the fluid volume to produce the second detection dataset.

In one embodiment, the method further comprises displaying the image of the biofield surrounding the living subject. In some embodiments, the method further comprises displaying the post-exposure image of the biofield surrounding the living subject.

In one embodiment, the baseline dataset is produced while the living subject is not disposed within the fluid volume. In some embodiments, the image of the biofield surrounding the living subject provides imaging information related only to the fluid volume surrounding the living subject, and does not provide imaging information related to anatomical details of the living subject.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. As used herein, unless explicitly stated otherwise, the term "or" is inclusive of all presented alternatives, and means essentially the same as the commonly used phrase "and/or." Thus, for example the phrase "A or B may be blue" may mean any of the following: A alone is blue, B alone is blue, both A and B are blue, and A, B and C are blue. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. A method of imaging a biofield surrounding a living subject, comprising the steps of:
    scanning a fluid volume with a nuclear magnetic resonance imaging system to produce a baseline dataset;
    positioning the living subject at least partially within the fluid volume;
    scanning the fluid volume with the nuclear magnetic resonance imaging system while the living subject is disposed within the fluid volume to produce a detection dataset;
    comparing the detection dataset to the baseline dataset with a computing system to produce a biofield dataset that includes spatially-encoded, discrete variations in observed transverse relaxation time and/or relaxation rate in the fluid volume; and
    generating, with the computing system, an image of the biofield surrounding the living subject from the biofield dataset, wherein the image of the biofield surrounding the living subject provides imaging information related only to the fluid volume surrounding the living subject, and does not provide imaging information related to internal anatomical details of the living subject.

2. The method of claim 1, further comprising:
    introducing one or more environmental factors into the fluid volume;
    scanning the fluid volume with the nuclear magnetic resonance imaging system while the living subject is disposed within the fluid volume to produce a second detection dataset;
    comparing the baseline dataset to the second detection dataset with the computing system to produce a second biofield dataset that includes discrete variations in observed transverse relaxation time and/or relaxation rate in the fluid volume; and
    generating, with the computing system, a post-exposure image of the biofield surrounding the living subject from the biofield dataset.

3. The method of claim 2, further comprising comparing the post-exposure image to the image of the biofield surrounding the living subject to detect biofield variances before and after the introduction of the one or more environmental factors into the fluid volume.

4. The method of claim 2, wherein the one or more environmental factors are selected from the group consisting of man-made electromagnetic fields, naturally occurring electromagnetic fields, gases, liquids, aerosols, solids, chemical compounds, minerals, fabrics, crystals, foods, and medications.

5. The method of claim 2, wherein the one or more environmental factors comprises a therapeutic and treatment modality.

6. The method of claim 2, further comprising displaying the post-exposure image of the biofield surrounding the living subject.

7. The method of claim 1, further comprising treating the fluid volume to increase a coherence of the fluid volume.

8. The method of claim 1, further comprising displaying the image of the biofield surrounding the living subject.

9. The method of claim 1, wherein the baseline dataset is produced while the living subject is not disposed within the fluid volume.

10. The method of claim 1, wherein the positioning the living subject step occurs after the scanning the fluid volume step.

* * * * *